United States Patent
Tovey et al.

[11] Patent Number: 5,928,244
[45] Date of Patent: Jul. 27, 1999

[54] TISSUE FASTENER IMPLANTATION APPARATUS AND METHOD

[75] Inventors: Ian J. Tovey, Bethel; Salvatore Castro, Seymour, both of Conn.

[73] Assignee: United States Surgical Corporation, Norwalk, Conn.

[21] Appl. No.: 08/953,584

[22] Filed: Oct. 17, 1997

Related U.S. Application Data

[63] Continuation of application No. 08/720,933, Oct. 4, 1996, abandoned.

[51] Int. Cl.$^6$ .................................................. A61B 17/56
[52] U.S. Cl. ............................................. 606/104; 606/72
[58] Field of Search .................................. 606/72, 73, 75, 606/76, 104

[56] References Cited

U.S. PATENT DOCUMENTS

| | | | |
|---|---|---|---|
| 2,121,193 | 6/1938 | Hanicke | 128/92 |
| 2,381,050 | 8/1945 | Hardinge . | |
| 2,489,870 | 11/1949 | Dzus | 606/73 |
| 2,490,364 | 12/1949 | Livingston . | |
| 2,579,438 | 12/1951 | Longfellow . | |
| 2,699,774 | 1/1955 | Livingston . | |
| 3,759,257 | 9/1973 | Fischer et al. . | |
| 3,760,802 | 9/1973 | Fischer et al. . | |
| 3,768,635 | 10/1973 | Eggert . | |
| 3,779,239 | 12/1973 | Fischer et al. . | |
| 3,782,374 | 1/1974 | Fischer . | |
| 3,805,775 | 4/1974 | Fischer et al. . | |

(List continued on next page.)

FOREIGN PATENT DOCUMENTS

| | | |
|---|---|---|
| 75330 | 3/1983 | European Pat. Off. . |
| 0077868 | 5/1983 | European Pat. Off. . |
| 0124489 | 11/1984 | European Pat. Off. . |
| 0232049 | 8/1987 | European Pat. Off. . |
| 0241240 | 10/1987 | European Pat. Off. . |
| 0238223 | 6/1988 | European Pat. Off. . |

(List continued on next page.)

OTHER PUBLICATIONS

Mitek G II Anchor, Mitek Surgical Products, Inc., 1991.
Mitek Anchor System, Mitek Surgical Products, Inc., 1990.
Mitek Quick Anchor, Mitek Surgical Products, Inc., 1990.
Statak Soft Tissue Attachment Device, Zimmer, Inc., 1988.
Tag Tissue Anchor Guide, Acufex Microsurgical, Inc., 1990.
Tag Tissue Anchor Rod Style Acufex Microsurgical, Inc., 1990.
Tag Tissue Anchor Wedge Style Acufex Microsurgical, Inc., 1990.
Rivet Joints in Aluminium Structural Components, Hoffer, 1983.
Raftopoulos, "A Proposed Design For An Expanding Hip Nail," Engineering in Medicine, vol. 11 (1982), pp. 187–188.
Design News, "Ligament Fastener Cuts Recovery Time," pp. 56–57, (1989).
Biomet Inc., "Ligament Screw System," 1990.

*Primary Examiner*—Michael Buiz
*Assistant Examiner*—David O. Reip

[57] ABSTRACT

An apparatus for applying a tissue fastener for fastening soft tissue to bone includes elongated members, one of which holds a loading unit having a tissue fastener mounted therein, and another of which is moved to expel the tissue fastener from the loading unit and expand legs of the tissue fastener to secure it within a predrilled hole in bone. The tissue fastener is preferably a two piece fastener including a body portion with legs flexibly expandable by a setting pin. The loading unit engages both the body and the setting pin.

16 Claims, 7 Drawing Sheets

U.S. PATENT DOCUMENTS

| | | | |
|---|---|---|---|
| 3,846,846 | 11/1974 | Fischer | 606/72 X |
| 3,910,281 | 10/1975 | Kletschka et al. | 128/335 |
| 3,951,261 | 4/1976 | Mandel et al. . | |
| 3,958,488 | 5/1976 | Fischer | 85/77 |
| 3,986,504 | 10/1976 | Avila | 128/92 |
| 4,006,747 | 2/1977 | Kronenthal et al. | 128/335 |
| 4,013,071 | 3/1977 | Rosenberg | 128/92 B |
| 4,091,806 | 5/1978 | Aginsky . | |
| 4,135,623 | 1/1979 | Thyen . | |
| 4,204,531 | 5/1980 | Aginsky . | |
| 4,227,518 | 10/1980 | Aginsky . | |
| 4,236,512 | 12/1980 | Aginsky . | |
| 4,244,370 | 1/1981 | Furlow et al. | 128/303 R |
| 4,259,072 | 3/1981 | Hirabayashi et al. | 433/173 |
| 4,262,665 | 4/1981 | Roalstad et al. | 128/92 BC |
| 4,275,717 | 6/1981 | Bolesky | 128/92 BC |
| 4,309,137 | 1/1982 | Tanaka et al. | 411/45 |
| 4,339,217 | 7/1982 | Lacey . | |
| 4,351,069 | 9/1982 | Ballintyn et al. | 3/1.912 |
| 4,409,974 | 10/1983 | Freedland | 128/92 B |
| 4,414,967 | 11/1983 | Shapiro | 128/92 B |
| 4,424,898 | 1/1984 | Thyen et al. . | |
| 4,453,539 | 6/1984 | Raftopoulos et al. | 128/92 BC |
| 4,454,875 | 6/1984 | Pratt et al. . | |
| 4,456,005 | 6/1984 | Lichty | 128/92 A |
| 4,474,517 | 10/1984 | Navoczynski | 411/45 |
| 4,483,678 | 11/1984 | Nishio et al. | 433/201 |
| 4,519,100 | 5/1985 | Wills et al. | 3/1.9 |
| 4,519,735 | 5/1985 | Mächtle . | |
| 4,520,511 | 6/1985 | Gianezio et al. | 3/1.913 |
| 4,539,981 | 9/1985 | Tunc | 128/92 B |
| 4,542,539 | 9/1985 | Rowe, Jr. et al. | 623/16 |
| 4,550,448 | 11/1985 | Kenna | 623/16 |
| 4,550,449 | 11/1985 | Tunc | 623/16 |
| 4,570,623 | 2/1986 | Ellison et al. . | |
| 4,586,502 | 5/1986 | Bedi et al. | 128/334 R |
| 4,590,928 | 5/1986 | Hunt et al. . | |
| 4,590,930 | 5/1986 | Kurth et al. | 128/92 BC |
| 4,591,048 | 5/1986 | Eldridge, Jr. . | |
| 4,596,503 | 6/1986 | Mirsberger et al. | 411/32 |
| 4,599,085 | 7/1986 | Riess et al. | 623/16 |
| 4,612,923 | 9/1986 | Kronenthal | 128/92 R |
| 4,621,640 | 11/1986 | Mulhollan et al. . | |
| 4,632,100 | 12/1986 | Somers et al. | 128/92 |
| 4,637,765 | 1/1987 | Omata . | |
| 4,640,271 | 2/1987 | Lower | 128/92 YF |
| 4,653,486 | 3/1987 | Coker | 128/92 YF |
| 4,655,777 | 4/1987 | Dunn et al. | 623/16 |
| 4,656,806 | 4/1987 | Leibhard et al. . | |
| 4,669,473 | 6/1987 | Richards et al. | 128/334 |
| 4,681,590 | 7/1987 | Tansley | 623/23 |
| 4,699,271 | 10/1987 | Lincoln et al. . | |
| 4,711,232 | 12/1987 | Fischer et al. . | |
| 4,713,076 | 12/1987 | Draenert | 623/16 |
| 4,716,893 | 1/1988 | Fischer et al. . | |
| 4,738,255 | 4/1988 | Goble et al. | 128/92 YF |
| 4,741,330 | 5/1988 | Hayhurst | 128/92 YF |
| 4,759,670 | 7/1988 | Linder et al. | 411/43 |
| 4,760,843 | 8/1988 | Fischer et al. . | |
| 4,767,248 | 8/1988 | Pratt | 411/45 |
| 4,776,328 | 10/1988 | Frey et al. | 128/92 VT |
| 4,776,329 | 10/1988 | Treharne . | |
| 4,778,468 | 10/1988 | Hunt et al. | 623/16 |
| 4,787,378 | 11/1988 | Sodhi . | |
| 4,790,303 | 12/1988 | Steffee | 128/924 M |
| 4,790,304 | 12/1988 | Rosenberg . | |
| 4,793,335 | 12/1988 | Frey et al. | 606/73 |
| 4,796,612 | 1/1989 | Reese | 128/92 YF |
| 4,806,053 | 2/1989 | Herb . | |
| 4,818,163 | 4/1989 | Bereiter et al. . | |
| 4,828,562 | 5/1989 | Kenna | 623/13 |
| 4,834,752 | 5/1989 | Van Kampen . | |
| 4,861,197 | 8/1989 | Calandra, Jr. . | |
| 4,870,957 | 10/1989 | Goble et al. . | |
| 4,871,289 | 10/1989 | Choiniere . | |
| 4,895,148 | 1/1990 | Bays et al. | 606/213 |
| 4,898,156 | 2/1990 | Gatturna et al. | 606/72 |
| 4,898,505 | 2/1990 | Froehlich . | |
| 4,899,743 | 2/1990 | Nicholson et al. | 606/139 |
| 4,921,383 | 5/1990 | Fischer . | |
| 4,927,421 | 5/1990 | Goble et al. . | |
| 4,938,760 | 7/1990 | Burton et al. | 600/29 |
| 4,946,468 | 8/1990 | Li | 606/232 |
| 4,963,144 | 10/1990 | Huene . | |
| 4,968,315 | 11/1990 | Gatturna | 606/72 |
| 4,969,887 | 11/1990 | Sodhi | 606/67 |
| 4,969,892 | 11/1990 | Burton et al. | 606/218 |
| 4,976,680 | 12/1990 | Hayman et al. | 600/7 |
| 4,976,715 | 12/1990 | Bays et al. | 606/77 |
| 4,988,351 | 1/1991 | Paulos et al. | 606/75 X |
| 5,002,550 | 3/1991 | Li | 606/139 |
| 5,011,473 | 4/1991 | Gatturna | 604/51 |
| 5,013,316 | 5/1991 | Goble et al. | 606/72 |
| 5,015,250 | 5/1991 | Foster | 606/147 |
| 5,036,862 | 8/1991 | Pohndorf | 128/784 |
| 5,037,422 | 8/1991 | Hayhurst et al. | 606/72 |
| 5,041,129 | 8/1991 | Hayhurst et al. | 606/232 |
| 5,046,513 | 9/1991 | Gatturna et al. | 128/898 |
| 5,053,047 | 10/1991 | Yoon | 606/223 |
| 5,071,420 | 12/1991 | Paulos et al. | |
| 5,076,746 | 12/1991 | Fischer et al. . | |
| 5,078,730 | 1/1992 | Li et al. | 606/228 |
| 5,080,543 | 1/1992 | Murphy | 411/60 |
| 5,084,050 | 1/1992 | Draenert | 606/77 |
| 5,085,545 | 2/1992 | Takahashi | 411/45 |
| 5,085,661 | 2/1992 | Moss | 606/139 |
| 5,100,405 | 3/1992 | McLaren | 606/72 |
| 5,100,417 | 3/1992 | Cerier et al. | 606/139 |
| 5,102,421 | 4/1992 | Anspach, Jr. | 606/232 |
| 5,122,133 | 6/1992 | Evans | 606/73 |
| 5,129,906 | 7/1992 | Ross et al. | 606/77 |
| 5,131,533 | 7/1992 | Alpern . | |
| 5,144,961 | 9/1992 | Chen et al. . | |
| 5,154,719 | 10/1992 | Cotrel | 606/73 |
| 5,156,616 | 10/1992 | Meadows et al. . | |
| 5,167,664 | 12/1992 | Hodorek . | |
| 5,167,665 | 12/1992 | McKinney . | |
| 5,176,682 | 1/1993 | Chow . | |
| 5,203,784 | 4/1993 | Ross et al. . | |
| 5,207,679 | 5/1993 | Li . | |
| 5,209,753 | 5/1993 | Biedermann et al. | 606/72 |
| 5,217,486 | 6/1993 | Rice et al. . | |
| 5,224,946 | 7/1993 | Hayhurst et al. | 606/72 |
| 5,236,445 | 8/1993 | Hayhurst et al. | 606/232 |
| 5,246,441 | 9/1993 | Ross et al. | 606/53 |
| 5,258,016 | 11/1993 | DiPoto et al. | 606/239 |
| 5,268,001 | 12/1993 | Nicholson et al. | 606/72 |
| 5,336,240 | 8/1994 | Metzler et al. . | |
| 5,354,298 | 10/1994 | Lee et al. . | |
| 5,423,860 | 6/1995 | Lizardi . | |
| 5,441,502 | 8/1995 | Bartlett . | |
| 5,480,403 | 1/1996 | Lee et al. | 606/72 |
| 5,522,844 | 6/1996 | Johnson . | |
| 5,531,699 | 7/1996 | Tomba et al. . | |
| 5,534,011 | 7/1996 | Greene, Jr. et al. . | |
| 5,584,860 | 12/1996 | Goble et al. . | |
| 5,628,751 | 5/1997 | Sander et al. | 606/104 |
| 5,643,320 | 7/1997 | Lower et al. . | |

| | | | | | | |
|---|---|---|---|---|---|---|
| 5,662,658 | 9/1997 | Wenstrom, Jr. . | | 4106823 | 6/1992 | Germany . |
| 5,667,513 | 9/1997 | Torrie et al. . | | 584855 | 12/1977 | U.S.S.R. . |
| 5,741,268 | 4/1998 | Schutz . | | 2084468 | 4/1982 | United Kingdom . |
| | | | | 2199914 | 7/1988 | United Kingdom . |
| | FOREIGN PATENT DOCUMENTS | | | 2266246 | 10/1993 | United Kingdom . |
| | | | | WO8504568 | 10/1985 | WIPO . |
| 0376641 | 7/1990 | European Pat. Off. . | | 8603666 | 7/1986 | WIPO . |
| 0464479 | 1/1992 | European Pat. Off. . | | WO8901767 | 3/1989 | WIPO . |
| 0464480 | 1/1992 | European Pat. Off. . | | 8909030 | 9/1989 | WIPO . |
| 0465910 | 1/1992 | European Pat. Off. . | | 8910096 | 11/1989 | WIPO . |
| 0504915 | 9/1992 | European Pat. Off. . | | 9204874 | 4/1992 | WIPO . |
| 0588671 | 3/1994 | European Pat. Off. . | | 9308747 | 5/1993 | WIPO . |
| 0630613 | 12/1994 | European Pat. Off. . | | WO95/15726 | 6/1995 | WIPO . |
| 739089 | 1/1933 | France . | | WO96/14798 | 5/1996 | WIPO . |
| 2622430 | 5/1989 | France . | | | | |

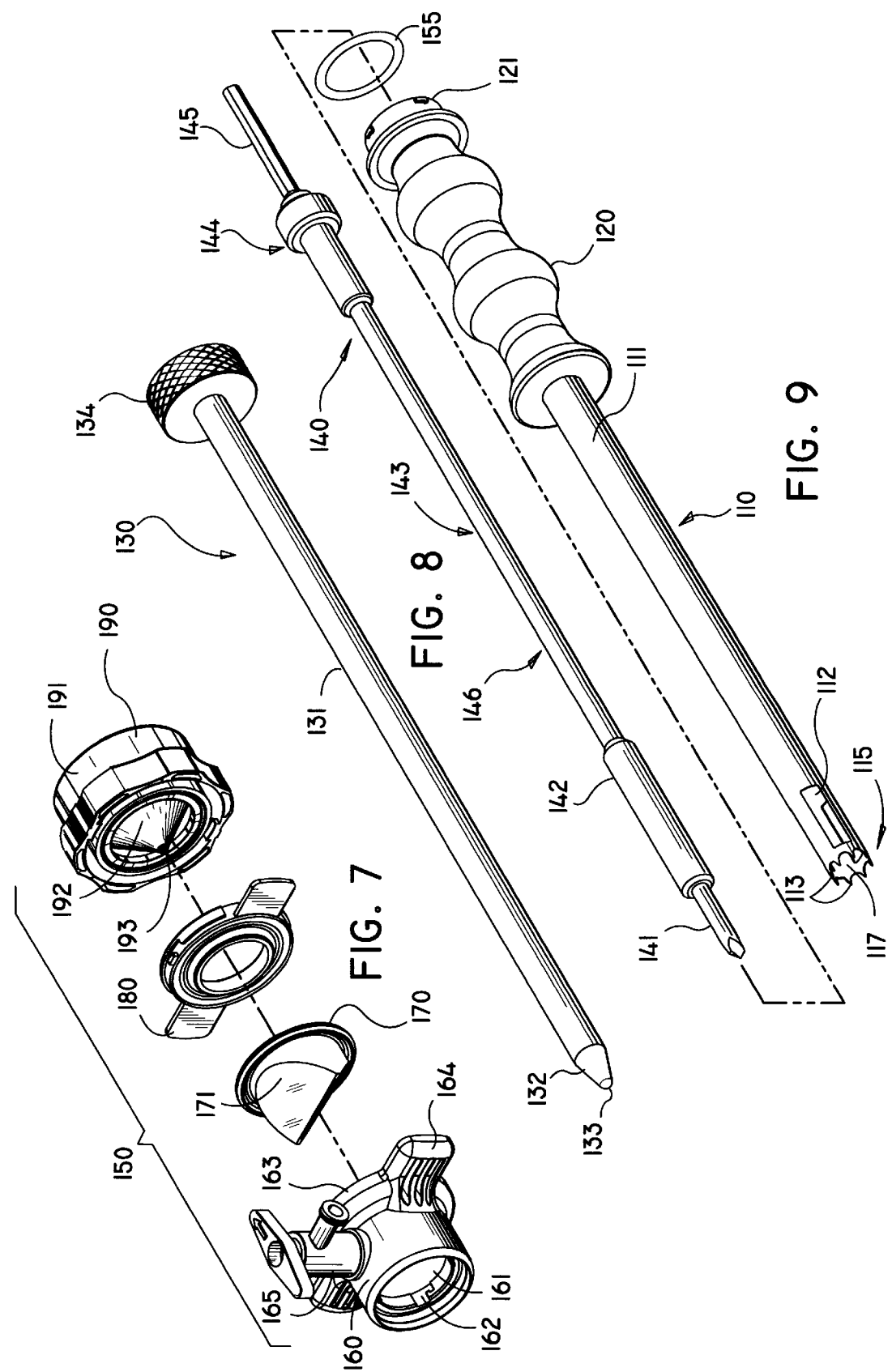

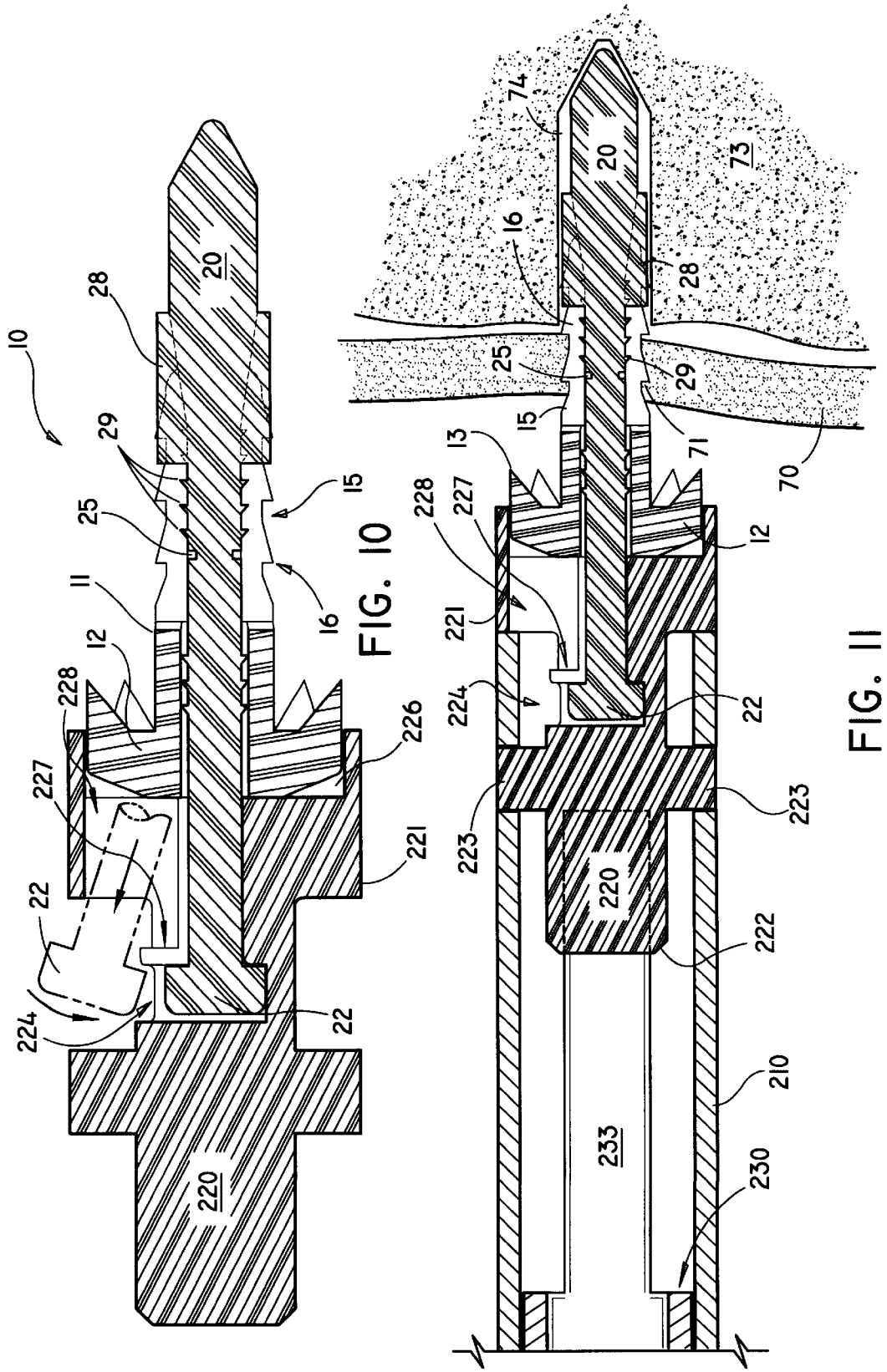

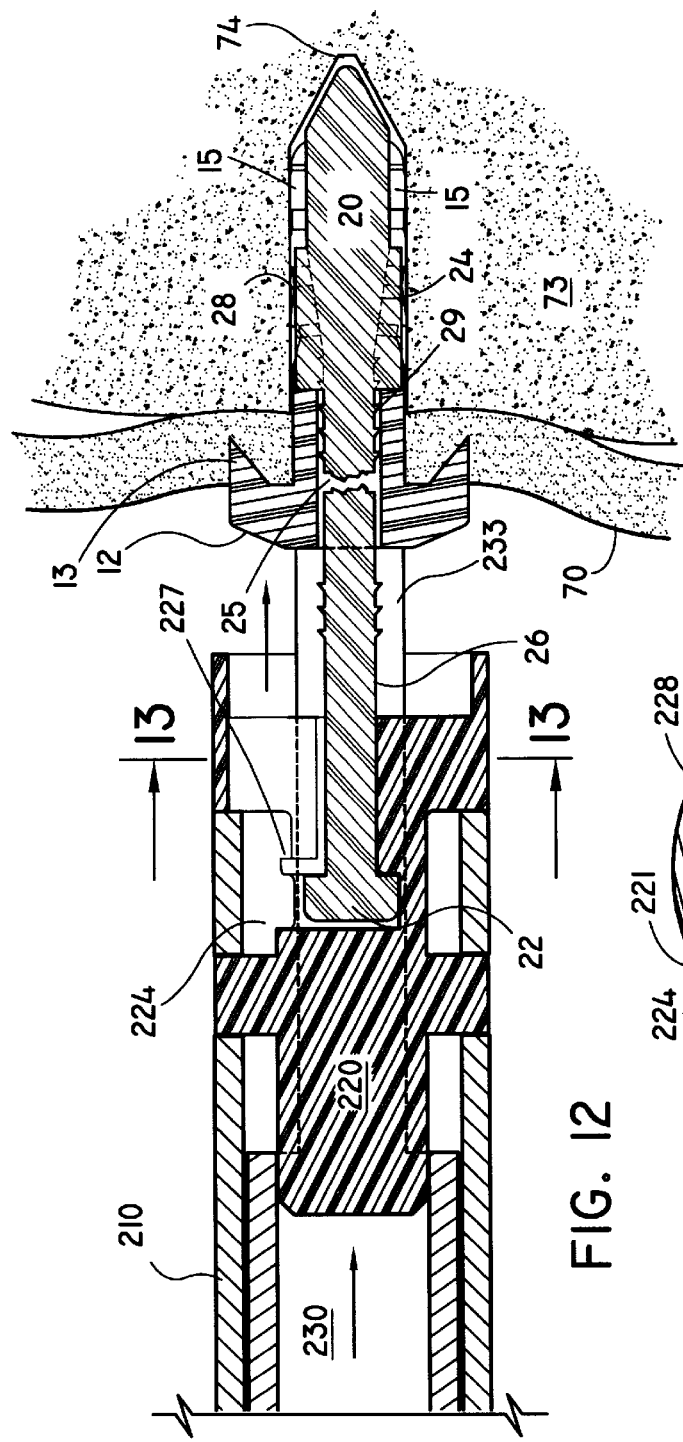
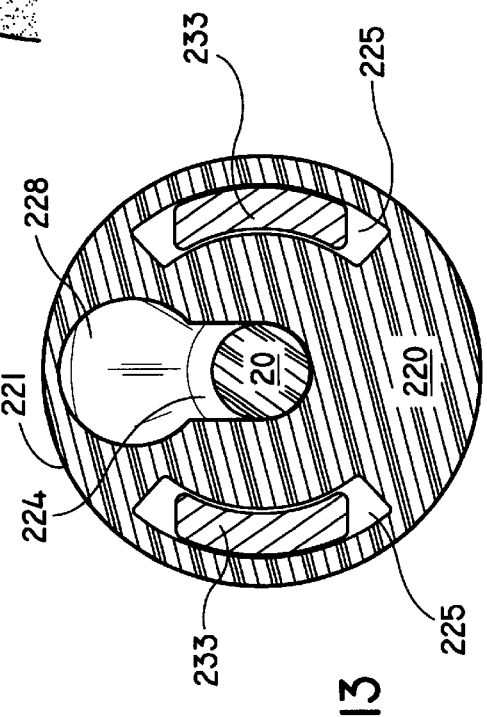
FIG. 12
FIG. 13

TISSUE FASTENER IMPLANTATION APPARATUS AND METHOD

This is a continuation of application Ser. No. 08/720,933 filed on Oct. 4, 1996, now abandoned.

BACKGROUND

1. Technical Field

The present disclosure relates to apparatus and methods for implanting tissue anchors and, more particularly, to apparatus and methods for implanting expandable tissue anchors.

2. Background of Related Art

During surgery it is often necessary to attach prosthetic implants or soft tissue such as muscle tissue, ligaments, or tendons to hard tissue such as bone. Various types of surgical fasteners are employed for accomplishing this function, including staples, screw and washer systems, suture anchoring devices, and tissue anchors.

The first of these types is illustrated in U.S. Pat. Nos. 4,454,875 and 4,570,623, which show metal staples with spikes on the underside of the crosspiece to secure ligaments.

Fasteners included in the second of these types are available as screw-washer combinations wherein the screw is fabricated from a surgically suitable metal, such as titanium or stainless steel alloy, and is usually of self tapping design. The washer can have distally pointing spikes and a central aperture through which the screw is disposed.

Suture anchors are adapted to be inserted into predrilled holes in bone and can be made of bioabsorbable material. U.S. Pat. No. 5,354,298 to Lee et al. discloses a two-piece suture anchor and an installation tool therefor. The suture anchor has a setting pin which is slidably connected to a socket having expandable legs. When the setting pin is retracted into the socket by being moved proximally (i.e. by pulling on the suture) the socket legs are radially splayed to secure the suture anchor in the hole in the bone.

Expandable tissue fasteners have bodies which directly fasten the soft tissue to bone, for example by means of a head portion with distally pointing teeth or spikes, rather than by means of a suture. For example, see U.S. Pat. No. 5,013,316 to Goble et al., which discloses a soft tissue anchor having a footing stud with self tapping threads for insertion into a hole in bone, and a tack portion which engages the footing stud. The tack portion has a broad head with spikes for securing soft tissue. U.S. Pat. No. 5,129,906 to Ross et al. discloses a cannulated bioabsorbable tack having annular ribs for attaching soft tissue to bone. Other fasteners include expandable portions which are inserted into a hole in bone and expanded therein to secure the fastener. For example, the fastener can include a body portion which is inserted into the bone and a setting pin which expands the body portion.

Expandable tissue fasteners adapted for use in minimally invasive surgical procedures (e.g. arthroscopic procedures) are employed, for example, in the repair of shoulder and knee injuries. In such procedures the operating instrumentation is usually deployed through a long, narrow cannula inserted through a small incision in the skin.

What is needed is an apparatus and method for conveniently applying an expandable tissue fastener, especially in minimally invasive surgical procedures.

SUMMARY

Apparatus is provided for implanting expandable tissue fasteners. The apparatus includes a handle portion, a first elongated member extending distally from the handle portion, an expandable tissue fastener mounting portion positioned adjacent a distal end of the first elongated member and configured to hold an unexpanded tissue fastener, and a second elongated member slidably mounted with respect to the first elongated member. The second elongated member is actuable from the handle portion for movement between a retracted first position and a fired second position wherein the second elongated member expels and expands the tissue fastener relative to the mounting portion.

The tissue fastener is preferably a two piece structure which includes a body having radially expandable legs and a setting pin disposed through a bore in the body and having a camming surface to expand legs of the body.

A system and method for implantation of the tissue fastener are also described herein.

BRIEF DESCRIPTION OF THE DRAWINGS

Various embodiments are described below with reference to the drawings wherein:

FIG. 7 is a perspective view of a cannula housing assembly for use with the apparatus of FIG. 5;

FIG. 8 is a perspective view of an obturator;

FIG. 9 is a perspective view showing a drill bit and drill guide;

FIG. 10 is an enlarged side cross sectional view showing the mounting of the tissue fastener to the tissue fastener mounting portion;

FIGS. 11 and 12 are enlarged side cross sectional views sequentially illustrating the implantation of the tissue fastener into a bone mass to secure soft tissue thereto; and FIG. 13 is an enlarged end cross sectional view taken at line 13—13 in FIG. 12 of the apparatus in accordance with a preferred embodiment of the subject disclosure.

DETAILED DESCRIPTION OF PREFERRED EMBODIMENTS

The preferred embodiments of the apparatus and methods disclosed herein are discussed in terms of orthopedic expandable tissue fastener implantation. It is also envisioned, however, that the disclosure is applicable to a wide variety of procedures including, but not limited to ligament repair, joint repair or replacement, non-union fractures, facial reconstruction, etc. In addition, it is believed that the present apparatus finds application in both open and minimally invasive procedures including endoscopic and arthroscopic procedures wherein access to the surgical site is achieved through a cannula or small incision.

In the description which follows, the term "proximal", as is traditional, will refer to the portion of the structure which is closest to the operator, while the term "distal" will refer to the portion which is furthest from the operator.

The apparatus and methods described herein are adapted for applying an expandable tissue fastener to a predrilled hole in bone. The orthopedic tissue fastener is preferably held in a disposable mounting unit.

Figure 1:
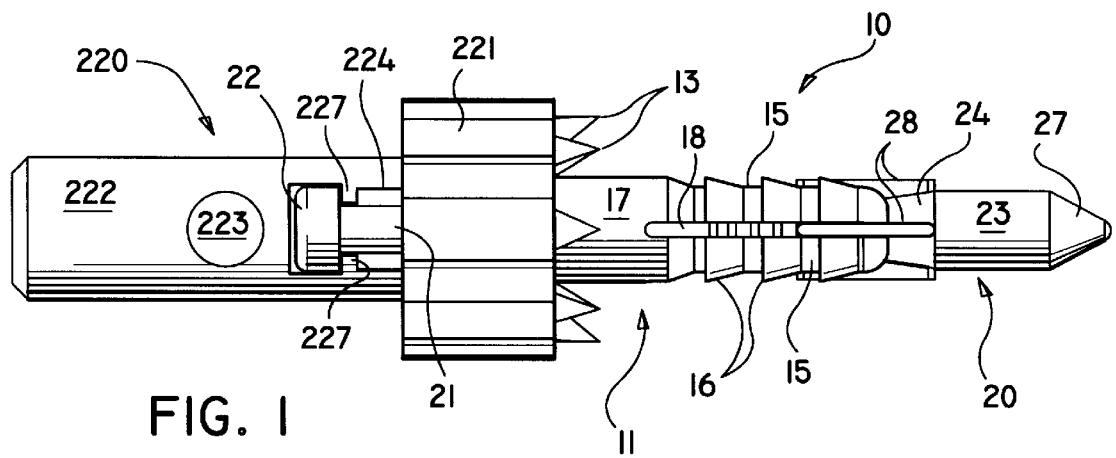
FIG. 1 is a side view of a tissue fastener mounting portion in accordance with a preferred embodiment of the subject disclosure with a tissue fastener mounted thereto.
Figure 2:
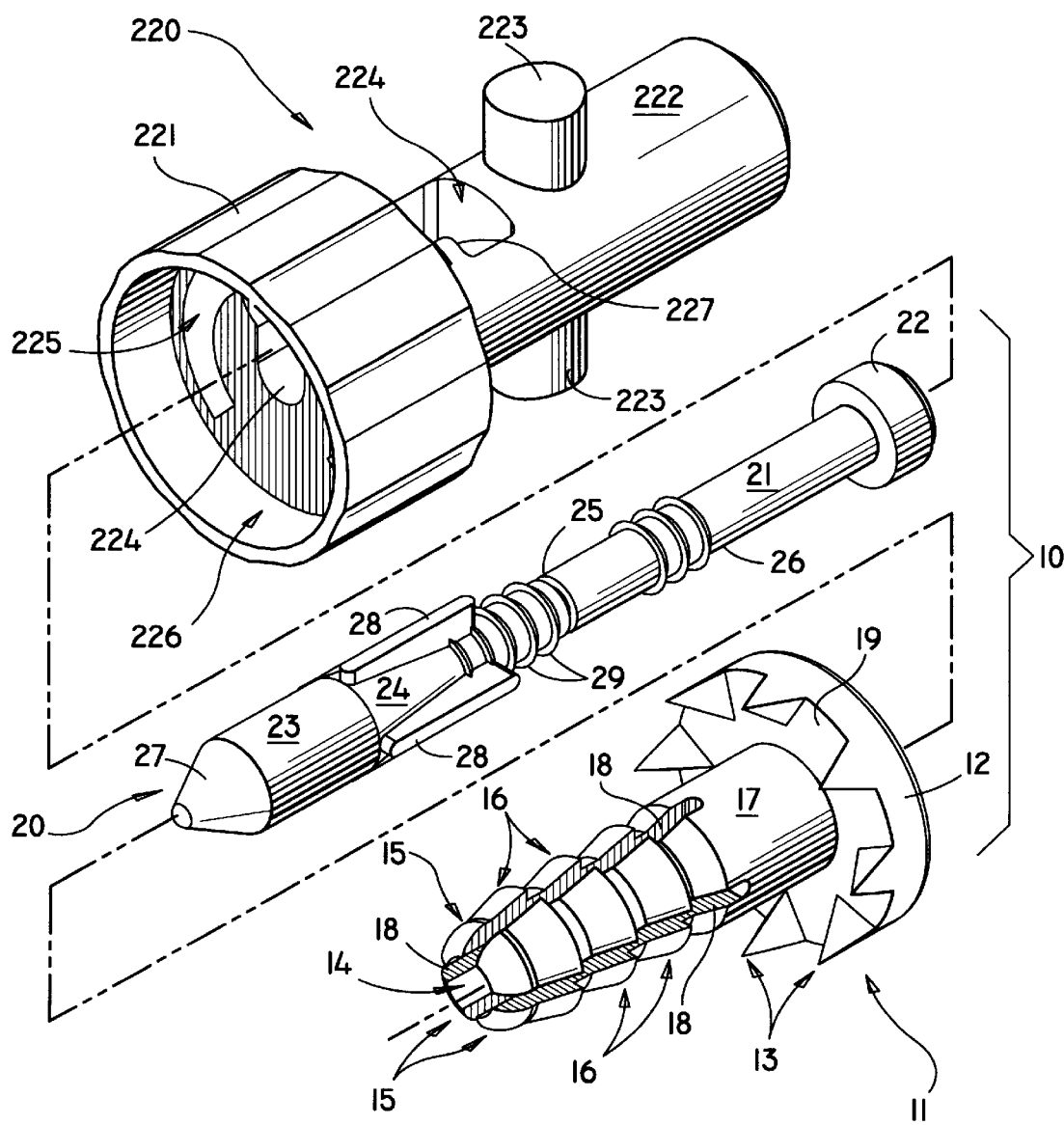
FIG. 2 is a perspective view with parts separated of the tissue fastener mounting portion of FIG. 1.
Figure 3:
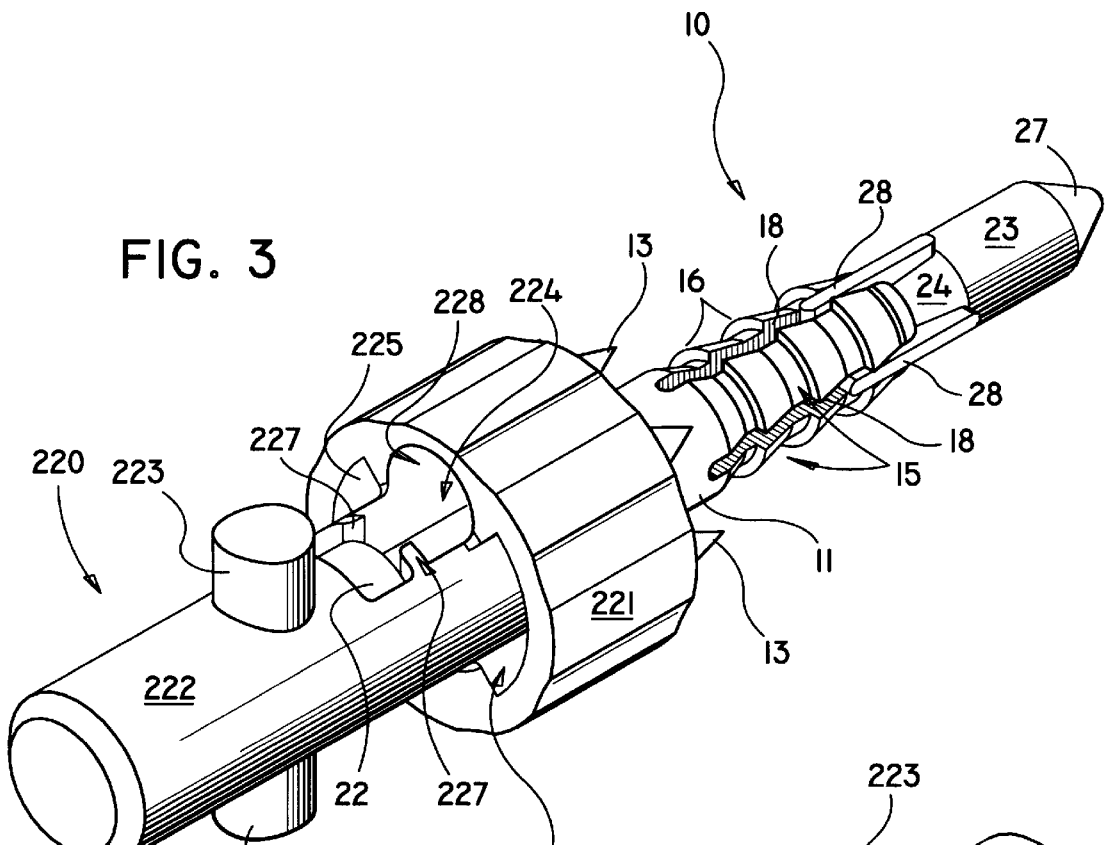
FIGS. 3 and 4 are front and rear enlarged perspective views of the tissue fastener mounting portion of FIG. 1.
Figure 4:
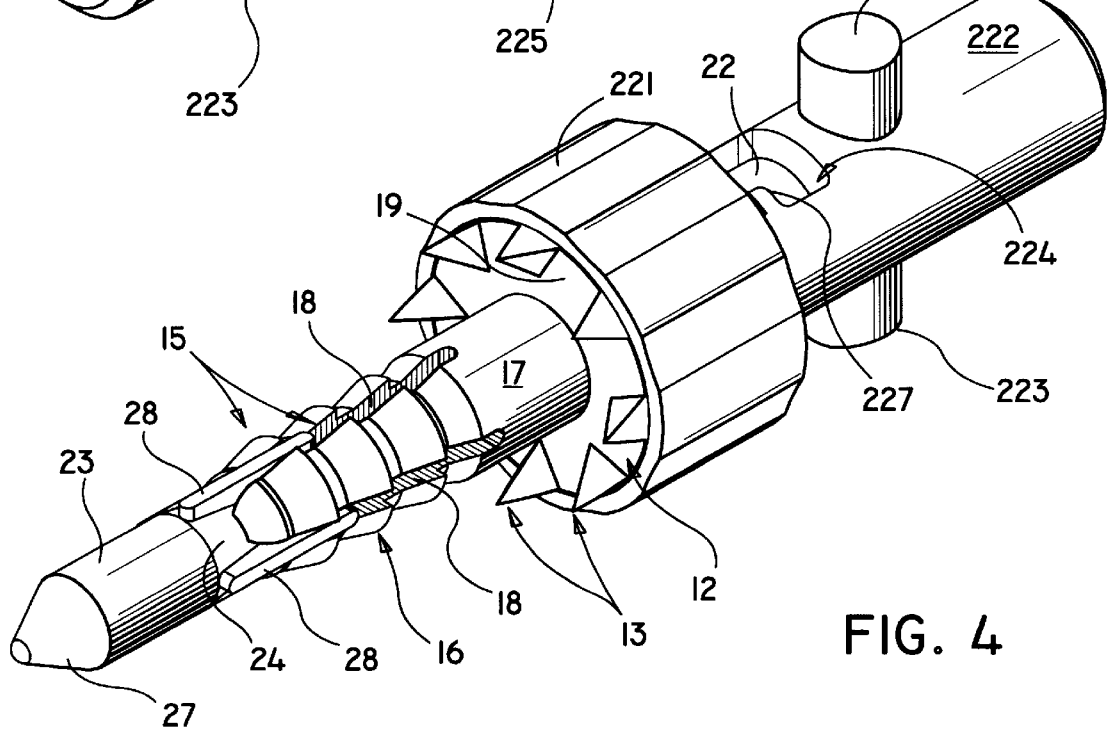

More particularly, referring now to FIGS. 1 and 2, the tissue fastener 10 includes an expandable body 11 with a tissue engaging head and a setting pin 20. More particularly, body 11 is a single piece member preferably fabricated from a bioabsorbable material such as polymers of glycolide, lactide, caprolactrone, p-dioxanone, trimethylene carbonate and physical and chemical combinations thereof. Body 11 includes a shaft 17 with an axial aperture 14 extending therethrough. Head 12 at the proximal end of shaft 17 includes a plurality of spaced apart distally pointing barbs, or spikes, 13 which are peripherally disposed around annular surface 19 of head 12.

Shaft 17 includes at least two, and preferably four distally extending legs 15 which are defined by lengthwise slots 18. Body 11 is fabricated from a material with sufficient flexibility and resiliency to allow legs 15 to radially expand by splaying outward. When body 11 is placed in a hole and legs 15 are expanded, barbs 16 on the outer surface of legs 15 engage the wall of bone tissue surrounding the hole and frictionally secure the body therein. Legs 15 are expanded in response to actuation by a setting pin as described below.

Setting pin 20 is part of expandable tissue fastener 10 and includes an elongated shaft 21 with at least one and preferably four lengthwise extending fins 28 adapted to engage slots 18 in body 11. A series of circumferential barbs 29 on the shaft 21 inhibit distal motion of setting pin 20 relative to body 11. Shaft 21 also includes a wider diameter head 22 at its proximal end to facilitate grasping of setting pin 20. At its distal end portion, shaft 21 includes an expanded diameter bulbous portion 23 which includes a proximally facing camming surface 24 and distally facing bevelled tip 27. Shaft 21 includes a proximal end portion 26 demarcated by a circumferential breakaway notch 25.

Shaft 21 of setting pin 20 is adapted to be slidably disposed within aperture 14 of body 11, as shown. When body 11 is moved distally with respect to setting pin 20, camming surface 24 eventually contacts the distal tips of legs 15. Further distal movement of body 11 causes legs 15 to splay apart under the camming action of surface 24 because the diameter of bulbous portion 23 is greater than that of aperture 14. Distal movement of body 11 can be effected by an instrument which distally advances body 11 while holding setting pin 20, or which grips and pulls the proximal portion 26 of the setting pin shaft while holding the body 11. At some point legs 15 are fully expanded and the setting pin 20 cannot move any further through aperture 14. Increased pulling force applied to the proximal end portion 26 of the shaft causes shaft 21 to fracture at breakaway notch 25 thereby splitting off the proximal end portion 26 when a predetermined force is applied. Setting pin 20 is configured and dimensioned such that when setting pin shaft 21 undergoes the controlled fracture at full expansion of legs 15, breakaway notch 25 will not be positioned outside aperture 14 of body 11. An expandable tissue fastener suitable for use in the apparatus and method described herein is disclosed and described in European Patent EPO 504 915 B1.

Referring to FIGS. 1 to 4, the disposable loading unit 220 is a tissue fastener mounting portion which is an independent structure for supporting both expandable body 11 of the tissue fastener and setting pin 20. The disposable loading unit 220 mounts to the distal end of the apparatus 200, as described below.

Disposable loading unit 220 includes a collar 221 defining a recess 226 into which head 12 of the body 11 is received and supported. Shaft 222 defines a lengthwise axis and includes laterally extending bayonet mounting pins 223 for engaging L-shaped slots 215 in housing tube 210 (discussed below). A mounting slot 224 for retaining setting pin 20 extends lengthwise through collar 221 and includes at least one abutment wall 227 for contacting and retaining head 22 of setting pin 20. An access port 228 enables head 22 to be mounted into mounting slot 224 proximal to abutment wall 227. Disposable loading unit 220 also includes arcuate lengthwise extending access chambers 225 which allow passage therethrough of pusher prongs 233 (discussed below) for contacting and pushing head 12 of the body 11.

Figure 5:
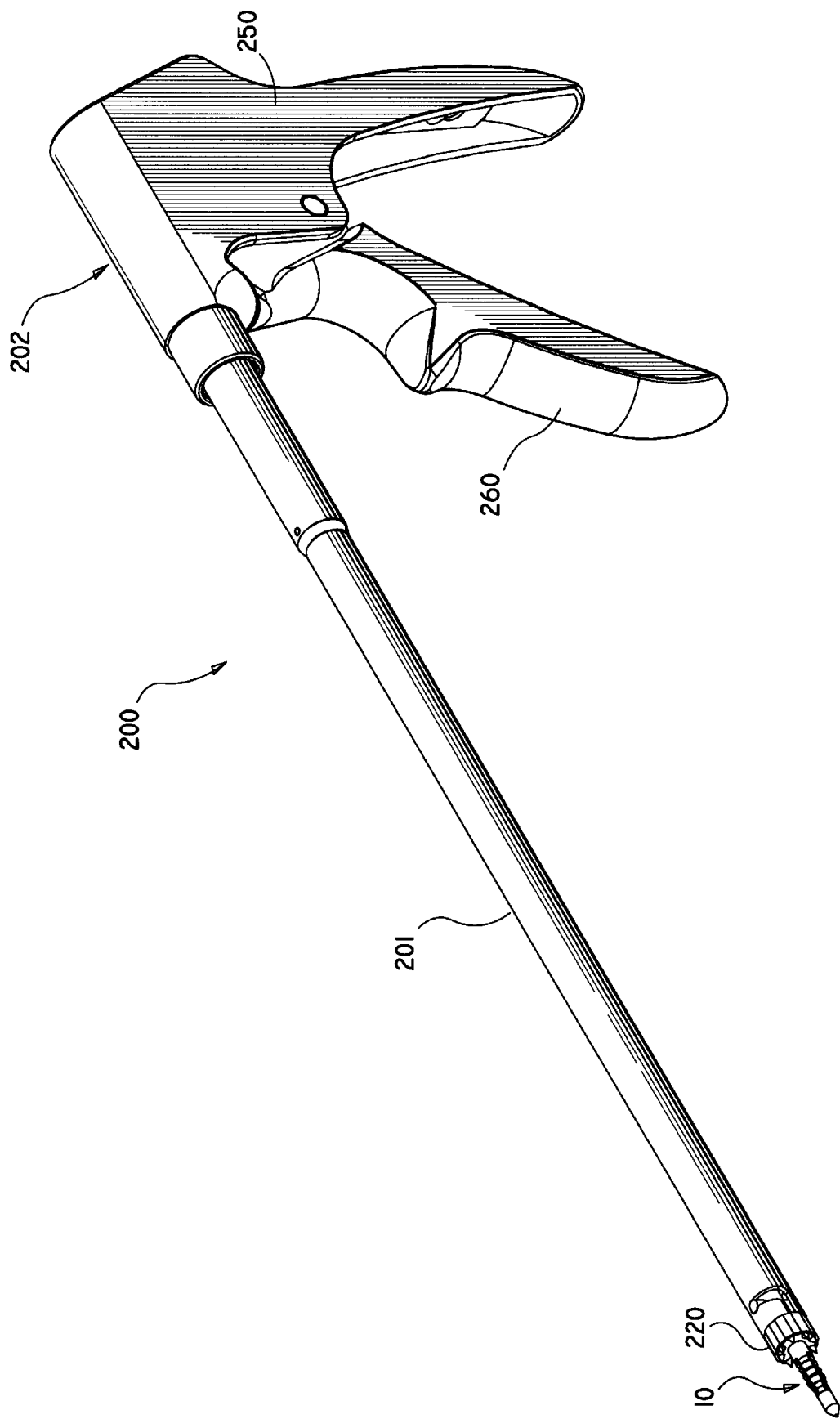
FIG. 5 is a perspective view of a tissue fastener implantation apparatus in accordance with a preferred embodiment of the subject disclosure.

Referring now to FIG. 5, in one embodiment tissue fastener implantation apparatus 200 of the subject disclosure includes an operating portion, i.e. elongated portion 201, and a handle portion 202 from which the operating portion is remotely actuated. Disposable loading unit 220, containing a tissue fastener 10, can be loaded to the distal end of operating portion 201 as shown. After the apparatus 200 is fired and tissue fastener 10 implanted, disposable loading unit 220 can be discarded and a fresh loading unit 220 mounted for a subsequent tissue fastener implantation.

Figure 6:
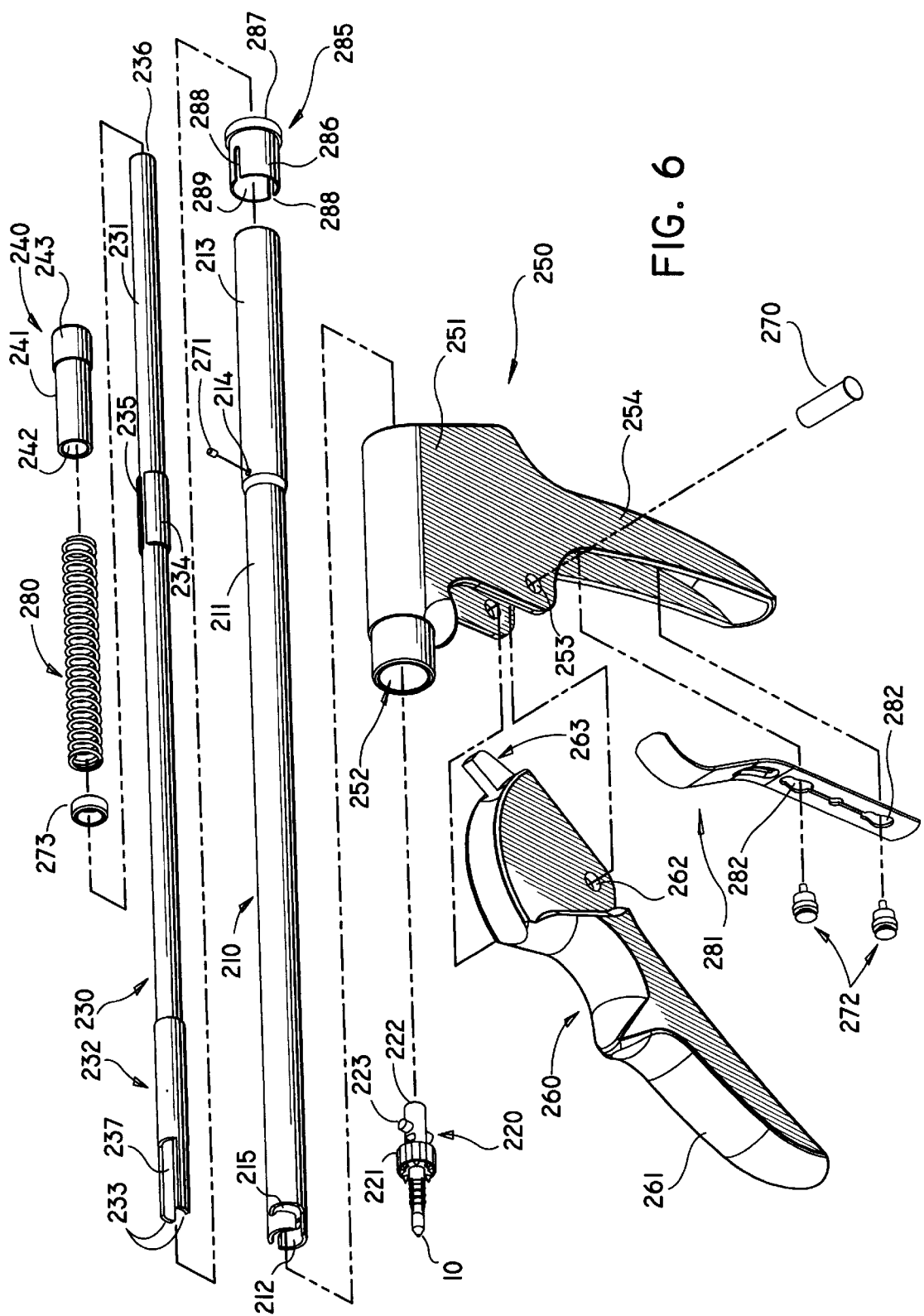
FIG. 6 is an exploded perspective view of the tissue fastener implantation apparatus of FIG. 5.

Referring now to FIGS. 5 and 6, operating portion 201 of the apparatus 200 includes a first elongated member defining a longitudinal axis which, in this embodiment, is an elongated housing tube 210 having a tubular body 211 with axial bore 212. At the distal end of the tubular body are at least one, and preferably two, L-shaped slots 215 which constitute a bayonet type mounting structure for engagement with the bayonet pins 223 of the disposable loading unit 220. The disposable loading unit 220 is preferably mounted in coaxial relationship to the apparatus 200. Housing tube 210 includes a wider diameter proximal portion 213 having a lateral aperture 214 for the reception therethrough of a brake pin 271. A housing holder 285 is fixedly mounted to the proximal end portion 213 of the housing tube 210 and is itself fixedly mounted within bore 252 of handle 250 to secure housing tube 210 to handle 250. Housing holder 285 includes a cylindrical portion 286 having a bore 289 through which the proximal end portion 213 of housing 210 is disposed. Housing holder 285 also includes a flange 287 and slots 288 extending lengthwise along the cylindrical portion 286.

A second elongated member in the operating portion 201, i.e. pusher rod 230, is slidably mounted with respect to the housing tube 210, preferably in a coaxial relationship. More particularly, in the present embodiment pusher rod 230 is slidably disposed within bore 212 of housing tube 210 preferably in a coaxial relationship. Pusher rod 230 includes a shaft 231, a distal portion 232 of slightly wider diameter than shaft 231, the distal portion 232 including at least one, and preferably two, distally extending pusher prongs 233, each preferably having an arcuate cross-section, prongs 233 being defined by longitudinal slots 237.

Pusher rod 230 includes a collar 234 having a slot 235 into which brake pin 271 extends. Proximal end 236 of the pusher rod is disposed within bore 242 of pusher knob 240. Pusher rod 230 is moved distally from an initial proximal position against the biasing force of helical compression spring 280 by a distally directed actuation force applied to pusher knob 240 by trigger 260, as will be further discussed below.

A retainer ring 273 is mounted on pusher rod 240 proximal to collar 234 against which retainer 273 abuts. Retainer 273 provides for retention of compression spring 280, which is mounted around the pusher rod proximal to retainer 273. At its other end, spring 280 abuts the distal edge of the cylindrical portion 241 of pusher knob 240.

Thus when a distal force is applied to pusher knob 240, pusher rod 230 is moved distally against the biasing force of compression spring 280. Brake pin 271 abuts the distal edge of retainer ring 273 thereby preventing it from distal advancement. Spring 280 is compressed between retainer ring 273 and pusher knob 240 as pusher rod 230 is advanced.

Handle 250 includes a frame 251 having a bore 252 into which the operating portion 201 is engaged. The frame 251 also includes a hand grip 254 and apertures 253 through which pivot pin 270 is disposed. A leaf spring 281 is mounted to the interior of hand grip 251 by means of leaf spring retainer bolts 272 disposed through apertures 282 in leaf spring 281. Leaf spring 281 contacts and biases the upper part of trigger 260 forward.

Trigger 260 includes an elongated body 261 pivotally connected to handle 250 at apertures 262 by means of pivot pin 270 disposed through apertures 253 in handle frame 251 and apertures 262 in trigger 260. Projection 263 extends upwardly from trigger 260 and abuts the proximal end 236 of pusher rod 230. When trigger 260 is pressed and pivoted about pin 270 projection 263 urges the pusher rod distally against the biasing action of spring 280.

Referring now to FIGS. 7, 8, and 9, an orthopedic tissue fastener implantation system includes a cannula housing assembly drill guide, drill bit, and obturator.

A cannula housing assembly suitable for use in the orthopedic tissue fastener implantation system is described in U.S. patent application Ser. No. 08/546,009 filed Oct. 20, 1995 and herein incorporated by reference.

Referring particularly now to FIG. 7, modular cannula housing assembly 150 includes a cylindrical base 160, a duckbill flange 170, a proximal housing element, and a seal assembly 190.

Molded cylindrical base 160 has a port opening 161 with a mounting fixture (e.g. bayonet mount) adapted to engage a corresponding mounting fixture of handle grip 120, a stopcock valve 165, and transversely extending grip portions 164 formed to extend from an annular flange 163 formed at the proximal end of cylindrical base 160.

The duckbill flange 170 is adapted to engage the proximal end opening of base 160 and includes a duckbill valve element 171.

Proximal housing element 180 is adapted to engage the proximal side of duckbill flange 170.

Seal assembly 190 includes a housing 191 and a seal member 192 having a central orifice 193.

Referring also now to FIG. 9, the cannula housing assembly 150 is adapted to engage the proximal end of handle grip 120. An O-ring 135 or other type gasket is provided to facilitate a gaseous sealing engagement between the cannula housing assembly 150 and the handle grip 120.

Drill guide 110 provides precise positioning of the drill for drilling a hole for the tissue fastener into the mass of bone tissue, and is a tubular body 111 having teeth 113 for gripping bone tissue at its distal end 115. Axial bore 117 in the drill guide is adapted to receive a drill bit 140. At least one, and preferably two or three, openings 112 in the vicinity of the distal end 115 permit the escape of bone fragments and shavings during the drilling operation and also provide means for visualizing the operating site. Drill guide 110 is preferably fabricated from a biocompatible metal such as stainless steel. A handle grip 120 is mounted externally around drill guide 110 to facilitate manipulation of drill guide 110. Handle grip 120 has a proximal end 121 which is adapted to engage port opening 161 of the cannula housing assembly with O-ring 155 interposed therebetween.

Drill bit 140 is used to create a hole of predetermined diameter in the mass of bone tissue. Drill bit 140 is a single piece member having a distal drilling tip 141, a shaft 146 having a relatively wide distal portion 142, a relatively narrow mid portion 143, and a proximal portion 144. A shank 145 extends proximally from proximal portion 144 of shaft 146 and is adapted to engage the chuck of a drilling machine (not shown). Drilling machines suitable for use in rotating the drill bit are well known and available to those with skill in the art. Drill bit 140 is adapted to fit into bore 117 of drill guide 110 and to be able to rotate therein.

Referring also now to FIG. 8, obturator 130 is part of the preferred expandable tissue fastener implantation system and includes a shaft 131 having a beveled tip with rounded point 133. A knurled knob 134 facilitates its handling and use to create a puncture opening in the soft body tissue overlying the bone with minimal damage to the body tissue.

Referring to FIG. 10, tissue fastener 10 can be mounted to disposable loading unit 220 by insertion of head 22 of setting pin 20 through access port 228, and then pivoting head 22 into the region of slot 224 proximal to the abutment wall 227. This assembly operation can be performed prior to packaging of the apparatus.

The operating site is prepared for tissue fastener placement in the following exemplary manner.

First, the cannula housing assembly 150 is mounted to handle grip 120 of drill guide 110. Obturator 130 is inserted through cannula housing assembly 150 and drill guide 110 such that tip 132 protrudes beyond distal end 115 of the drill guide.

Second, an incision is created in the skin to achieve access to body tissue surrounding the bone at the operating site. Cannula 150 is inserted into the incision.

The obturator 130 and drill guide 110 are both inserted through the incision and into the body tissue to create a passageway through the soft tissue to access the bone.

The obturator 130 is then removed leaving the drill guide 110 inserted through the passageway in the soft tissue with distal teeth 113 placed against the bone at the site to be drilled.

The drill bit 140 is then inserted through the drill guide and is used to create a hole in the bone.

The drill bit 140 and drill guide 110 are removed from drill guide 110 and the distal end of the apparatus 200 is then inserted into the drill guide 110.

Referring now to FIG. 11, the tissue fastener 10 is inserted through opening 71 in body tissue 70 and positioned such that distal portion 23 is within hole 74 in bone 73. Body 11 is initially in an unexpanded configuration and barbs 13 are not in full engagement with soft body tissue 70. Referring to FIGS. 12 and 13, when trigger 260 is pulled, pusher rod 230 moves distally, thereby advancing prongs 233 through slots 225 and into contact with head 12 of the body 11. Further advancement of prongs 233 forces the body 11 to move distally while setting pin 20 is held stationary with respect to the apparatus 200. As the body 11 advances distally into the hole 74, legs 15 contact the proximal camming surface 24 of the setting pin 20 and are moved into a splayed or radially expanded configuration, thereby frictionally engaging barbs 16 with the walls of hole 74. Barbs 13 are moved into full engagement with soft tissue 70 and hold soft tissue 70 in intimate contact with bone 73 to promote attachment thereto during the healing process. When a sufficient force has been applied to body 11 by prongs 233, the setting pin 20 fractures at the breakaway notch 25 within aperture 14. Barbs 29 on the setting pin resist the proximal movement of the body with respect to the setting pin, and insure that the body remains firmly engaged.

The apparatus 200 can then be withdrawn, and with it proximal portion 26 of setting pin shaft 21. The spent disposable loading unit 220 can be easily removed and a fresh one installed for a subsequent tissue fastener placement. A series of tissue fasteners can be applied to firmly secure the soft tissue 70 to bone 73.

It will be understood that various modifications may be made to the embodiments disclosed herein. For example, instead of distally advancing the body 11 while holding the setting pin 20 stationary, the apparatus can hold body 11 stationary while proximally pulling the setting pin 20. The above description should not be construed as limiting, but merely as exemplifications of preferred embodiments. Those skilled in the art will envision other modifications within the scope and spirit of the claims appended hereto.

What is claimed is:

1. An apparatus for implanting expandable tissue fasteners comprising:
   a handle portion comprising a fixed handle and a pivotable trigger;
   a first elongate member extending distally from the handle portion and defining a longitudinal axis;
   an expandable tissue fastener mounting portion configured for detachable connection to a distal end of the first elongate member and configured to hold an unexpanded tissue fastener; and
   a second elongate member slidably mounted with respect to the first elongate member and remotely actuable by the pivotable trigger for movement between a retracted first position and a fired second position whereby the second elongate member expels and expands an expandable tissue fastener relative to the mounting portion.

2. An apparatus as in claim 1 wherein the second elongate member is mounted within an axial bore of the first elongate member.

3. An apparatus as in claim 1 wherein the expandable tissue fastener mounting portion is configured to hold an unexpanded expandable tissue fastener in coaxial alignment with the longitudinal axis of the first elongate member.

4. An apparatus as in claim 3 wherein the expandable tissue fastener mounting portion is configured such that a distal portion of an expandable tissue fastener extends from a distal end of the expandable tissue fastener mounting portion.

5. An apparatus for implanting expandable tissue fasteners comprising:
   a handle portion comprising a fixed handle and a pivotable trigger;
   a first elongate member connected to the handle portion and defining a longitudinal axis, the first elongate member having a distal end defining mounting structure for detachably receiving an expandable tissue fastener mounting portion; and
   a second elongate member slidably mounted with respect to the first elongate member and remotely actuable by the pivotable trigger for movement between a retracted first position and a fired second position.

6. An apparatus as in claim 5 further comprising an expandable tissue fastener mounting portion having a proximal end and a distal end, the proximal end having mounting structure for releasably engaging the corresponding mounting structure on the distal end of the first elongate member.

7. An apparatus as in claim 6 further comprising an expandable tissue fastener mounted in the expandable tissue fastener mounting portion.

8. An apparatus for implanting expandable tissue fasteners comprising:
   a handle portion comprising a fixed handle and a pivotable trigger;
   a first elongate tubular member connected to the handle portion and defining a longitudinal axis;
   an expandable tissue fastener mounting portion configured for detachable connection to a distal end of the first elongate tubular member and configured to independently support an unexpanded expandable tissue fastener; and
   a second elongate tubular member coaxially slidable within the first tubular member and remotely actuable from the handle portion for movement between a retracted first position and a fired second position whereby the second elongate tubular member simultaneously expels and expands an expandable tissue fastener relative to the mounting portion.

9. An apparatus as in claim 8 wherein the first elongate tubular member includes mounting structure at a distal end thereof and a proximal portion of the expandable tissue fastener mounting portion includes corresponding mounting structure for releasably engaging the mounting structure on the distal end of the first elongate tubular member.

10. An apparatus as in claim 8 wherein the expandable tissue fastener mounting portion defines at least one longitudinal channel therethrough and the second elongate tubular member includes pusher structure on a distal end thereof, the pusher structure slidable through the channel to engage an expandable tissue fastener.

11. An apparatus as in claim 10 wherein the expandable tissue fastener mounting portion defines a pair of radially spaced channels and the pusher structure includes a pair of projections longitudinally aligned with the radially spaced channels for movement therethrough to engage an expandable tissue fastener.

12. An apparatus as in claim 8 further comprising an unexpanded expandable tissue fastener independently supported in the expandable tissue fastener mounting portion.

13. In an apparatus for implanting expandable tissue fasteners of the type having a body portion and a coaxially slidable setting pin, the improvement comprising a handle portion, an expandable tissue fastener mounting portion for supporting both a body portion and a setting pin and an actuation member for moving a body portion distally relative to a setting pin for expanding the expandable tissue fastener.

14. A method for implanting an expandable tissue fastener to join tissues comprising the steps of:
   providing an apparatus for implanting expandable tissue fasteners, the apparatus having a handle, an expandable tissue fastener mounting portion having an expandable tissue fastener including a body and a setting pin supported therein, and an actuation member for expanding the expandable tissue fastener;

preparing an operating site at which the tissues are to be fastened;

contacting the tissues to be fastened;

positioning the expandable tissue fastener at the operating site; and actuating the actuation member of the apparatus to drive the body of the expandable fastener distally relative to the setting pin.

15. An expandable tissue fastener mounting portion comprising:

a frame defining a longitudinal axis and having a proximal end, a distal end and an intermediate portion;

mounting structure formed adjacent the proximal end configured to engage corresponding mounting structure formed on an apparatus for implanting expandable tissue fasteners;

first expandable tissue fastener supporting structure formed adjacent the distal end and configured to support a body of an expandable tissue fastener; and second expandable tissue fastener supporting structure formed adjacent the intermediate portion of the frame and configured for locking engagement with a head of a setting pin of an expandable tissue fastener.

16. An expandable tissue fastener mounting portion as in claim 15 further comprising an expandable tissue fastener having a body and a setting pin mounted therein.

* * * * *